United States Patent
Ikushima et al.

(10) Patent No.: US 7,494,539 B2
(45) Date of Patent: Feb. 24, 2009

(54) PRODUCTION METHOD OF DENTAL CERAMICS MATERIAL

(75) Inventors: Keisuke Ikushima, Itabashi-ku (JP); Shuji Aoyagi, Itabashi-ku (JP)

(73) Assignee: GC Corporation, Tokyo (JP)

( * ) Notice: Subject to any disclaimer, the term of this patent is extended or adjusted under 35 U.S.C. 154(b) by 207 days.

(21) Appl. No.: 11/668,264

(22) Filed: Jan. 29, 2007

(65) Prior Publication Data

US 2007/0182042 A1 Aug. 9, 2007

(30) Foreign Application Priority Data

Feb. 8, 2006 (JP) ............................... 2006-031149

(51) Int. Cl.
*C04B 35/48* (2006.01)
*A61C 5/09* (2006.01)

(52) U.S. Cl. .......................... 106/35; 501/103; 501/105

(58) Field of Classification Search ................. 501/105, 501/103; 106/35
See application file for complete search history.

(56) References Cited

FOREIGN PATENT DOCUMENTS

| DE | 42 07 179 A1 | 9/1992 |
|---|---|---|
| JP | 2571646 | 10/1996 |
| JP | 2004-527280 | 9/2004 |
| WO | WO 01/12097 A1 | 2/2001 |
| WO | WO 2005/070322 A1 | 8/2005 |

*Primary Examiner*—C. Melissa Koslow
(74) *Attorney, Agent, or Firm*—Oblon, Spivak, McClelland, Maier & Neustadt, P.C.

(57) ABSTRACT

To make a color tone similar to that of dentin of a tooth at a low cost without discoloration when baking, a dental ceramics material is produced by: mixing a pink coloring agent and a yellow coloring agent with zirconium oxide containing a stabilizer while having a mixing ratio of 0.001 to 5 wt. % respectively; and baking it, where the pink coloring agent is obtained by dissolving manganese oxide in aluminum oxide as a solid solution, the yellow coloring agent is obtained by dissolving vanadium oxide in zirconium oxide as a solid solution, the zirconium oxide contains 0.1 to 30 wt. % aluminum oxide if necessary, the stabilizer is one or more kinds selected from a group including yttrium oxide, magnesium oxide, calcium oxide, and cerium oxide, and the content thereof is preferably 3 to 7 wt. %.

4 Claims, No Drawings

PRODUCTION METHOD OF DENTAL CERAMICS MATERIAL

BACKGROUND OF THE INVENTION

1. Field of the Invention

The present invention relates to a production method of a dental ceramics material capable of expressing a color tone similar to that of dentin of a tooth easily at a low cost.

2. Description of the Conventional Art

Transparency of a human tooth is gradually decreased from enamel which is a surface layer to dentin inside the enamel in general. When a dental technician produces a dental prosthesis, a material having transparency is used on the surface side and a material having low transparency and chroma is used at the inside in order to make a color tone similar to a natural tooth.

In recent years, when a dental prosthesis is produced by a ceramics material, stabilized zirconium oxide is often used for a ceramics frame to be an inner cap such as a crown, a bridge or the like, and for a ceramics abutment which is a material for penetrating a gingival part of a dental implant, since stabilized zirconium oxide has high strength. However, since zirconium oxide is white and opaque, the ceramics frame and the ceramics abutment are visible when the material having high transparency is built on the surfaces of the ceramics frame and the ceramics abutment. So, it is not preferable aesthetically. In order to avoid this problem, a large amount of opaquers must be used before the material is built on the surface, and excessive skill is required.

Further, when the dental prosthesis is produced by a ceramics, the material having transparency is built on the surface of the ceramics frame and the ceramics abutment and baked at 1,350 to 1,600 degrees C. Thus, there is a problem that a coloring agent which has been conventionally used in a dental field is decomposed so as not to express an intended color tone.

On the other hand, a colored sintered zirconium oxide has been proposed (for example, refer to Japanese translation of PCT international application No. 2004-527280, Section Nos. 0037 and 0040). In order to produce the sintered zirconium oxide, a coloring oxidizer having an element of a group including Pr, Er, Fe, Co, Ni, Ti, V, Cr, Cu and Mn is preferably contained as a coloring agent, and $Fe_2O_3$, $Er_2O_3$, and $MnO_2$ are preferable used. However, since this coloring agents must be added in a form of an oxide obtained by dissolving in HCl, the color may be damaged when the coloring agents are baked at 1,350 to 1,600 degrees C. Further, when the above-described various coloring agents are combined to be used, there are many agents which hardly obtain a color tone of dentin of a tooth which is required in a dental filed. Further, since the coloring agents must be added as a form of an oxide obtained by dissolving in HCl, a raw material having remarkably high cost must be used. So, there is a problem of production cost.

Further, a method for blending $Er_2O_3$, $Pr_6O_{11}$, $Fe_2O_3$ and ZnO to zirconium oxide containing a stabilizer so as to color dentin has been proposed (for example, refer to Japanese Patent No. 2571646). However, there is a problem that $Er_2O_3$ and the like cannot be well mixed without blending as a solution which is once dissolved by hydrochloric acid or nitric acid. Thus, $Er_2O_3$ and the like are necessarily mixed by the steps of pre-baking a powder obtained from the solution, and sintering with adding and mixing an iron compound and a zinc compound. So, the use of $Er_2O_3$ and the like is troublesome and complicated. Further, when $Er_2O_3$, $Pr_6O_{11}$ are used, these are decomposed at about 1,300 degrees C. Thus, there is a problem that $Er_2O_3$, $Pr_6O_{11}$ cannot be used at 1,350 to 1,600 degrees C. which is a baking temperature of zirconium oxide containing a general stabilizer.

SUMMARY OF THE INVENTION

An objective of the present invention is to provide a production method of a dental ceramics material capable of easily expressing a delicate color tone of dentin of a tooth, in which the ceramics material is not discolored when baking at a high temperature.

The earnest work was carried out in order to solve the above-mentioned problems and, as a result of this, the followings were found out to complete the present invention. A dental ceramics material capable of easily expressing a delicate color tone of dentin of a tooth can be produced by mixing a pink coloring agent and a yellow coloring agent with zirconium oxide containing the stabilizer at a specified range of ratio respectively, and baking it, where the pink coloring agent is obtained by dissolving manganese oxide in aluminum oxide as a solid solution, and the yellow coloring agent is obtained by dissolving vanadium oxide in zirconium oxide as a solid solution.

That is, the present invention relates to a production method of a dental ceramics material, the method comprising: mixing a pink coloring agent and a yellow coloring agent at a mixing ratio of 0.001 to 5 wt. % respectively with zirconium oxide containing a stabilizer, and baking it so as to produce a dental ceramics material, where the pink coloring agent is obtained by dissolving manganese oxide in aluminum oxide as a solid solution, and the yellow coloring agent is obtained by dissolving vanadium oxide in zirconium oxide as a solid solution.

Further, if the zirconium oxide containing the stabilizer contains 0.1 to 30 wt. % aluminum oxide, strength of the ceramics material is increased after baking. So, it is preferable.

Further, it is preferable that the stabilizer is one or more kinds selected from a group including yttrium oxide, magnesium oxide, calcium oxide, and cerium oxide, and the content is preferably 3 to 7 wt. %.

According to a production method of a dental ceramics material according to the present invention, a dental ceramics material capable of easily expressing a delicate color tone of dentin of a tooth can be produced without discoloring when it is baked at a high temperature.

DETAILED DESCRIPTION OF PREFERRED EMBODIMENT

That is, the present invention relates to a production method of a dental ceramics material, the method comprising: mixing a pink coloring agent and a yellow coloring agent at a mixing ratio of 0.001 to 5 wt. % respectively with zirconium oxide containing the stabilizer, and baking it so as to produce a dental ceramics material, where the pink coloring agent is obtained by dissolving manganese oxide in aluminum oxide as a solid solution, and the yellow coloring agent is obtained by dissolving vanadium oxide in zirconium oxide as a solid solution.

In the production method of a dental ceramics material according to the present invention, a stabilizer contained in zirconium oxide which is a primary material is one or more kinds selected from a group including yttrium oxide, magnesium oxide, calcium oxide, and cerium oxide, and the content is preferably 3 to 7 wt. %. If the content of the stabilizer is less than 3 wt. %, the stabilizing effect to zirconium oxide cannot be obtained, and if the content is more than 7 wt. %, toughness is decreased, so that it is not preferable.

Further, when zirconium oxide containing the stabilizer which is a primary material contains aluminum oxide and the content of the aluminum oxide is 0.1 to 30 wt. %, strength of the ceramics material is increased after baking. So, it is preferable. If the content of aluminum oxide is less than 0.1 wt. %, the effect for increasing strength after baking cannot be obtained. If the content is more than 30 wt. %, the content of aluminum oxide is increased too much, and thus the content of zirconium oxide containing a stabilizer which is a primary material is relatively decreased so as to decrease the strength. So, it is not preferable.

In the present invention, the pink coloring agent obtained dissolving manganese oxide in aluminum oxide as a solid solution, and the yellow coloring agent obtained by dissolving vanadium oxide in zirconium oxide as a solid solution are mixed with these primary materials at a mixing ratio of 0.001 to 5 wt. % respectively, and are baked so as to produce a dental ceramics material.

The reason of using these materials is as follows. Since the pink coloring agent is obtained by dissolving manganese oxide in aluminum oxide as a solid solution, and the yellow coloring agent is obtained by dissolving vanadium oxide in zirconium oxide as a solid solution, these coloring agents are not decomposed when being baked at 1,350 to 1,600 degrees C., and further, these coloring agents can be added into the primary material in a powdery state. Thus, the material can be colored without using an ionic solution which makes the material being high cost. Further, each content of the agents is within a range of 0.001 to 5 wt. %. If the content is less than 0.001 wt. %, the desired coloring effect cannot be obtained, and if the content is more than 5 wt. %, a coloring tone where the agent contains more than 5 wt. % is increased, so as to widely differ from a color tone of dentin of a tooth.

Further, present inventors also confirmed the followings. When a coloring agent in which manganese oxide is not dissolved in aluminum oxide as a solid solution and a coloring agent in which vanadium oxide is not dissolved in zirconium oxide as a solid solution are mixed with zirconium oxide containing the stabilizer and baked at 1,350 to 1,600 degrees C., the coloring agents are decomposed so as to produce a white prosthesis. Thus, it is not preferable aesthetically.

When a ceramics frame or a ceramics abutment is produced using the dental ceramics material produced by the production method of the dental ceramics material according to the present invention, the following two methods can be used.

One method comprises the steps of: mixing desired amounts of the pink and yellow coloring agents with the primary material, which is obtained by mixing aluminum oxide with zirconium oxide containing the stabilizer if necessary; mixing an organic binder such as acrylic acid ester or the like with the mixed material; pressing the material by a press machine so as to form a green body; heating up to a specified temperature by a specified heating rate so as to remove the organic content; pre-baking; attaching to a specific pedestal of a CAD/CAM device or the like; grinding to have an external shape of the ceramics frame or the ceramics abutment; and baking. In this method, there can be taken the steps of: attaching the green body, in which the organic content is removed, to the specific pedestal of the CAD/CAM device or the like after baking instead of pre-baking; and grinding it to have an external shape of the ceramics frame or the ceramics abutment. Further, of course, the coloring agent can be added after the binder is mixed beforehand with zirconium oxide.

Another method comprises the steps of: producing beforehand a gypsum model of the inside of an oral cavity using an impression taken out from the inside of an oral cavity of a patient; mixing desired amounts of the pink and yellow coloring agents with a primary material, which is obtained by mixing aluminum oxide with zirconium oxide containing a stabilizer if necessary; spraying the mixed materials, in which an organic binder such as acrylic acid ester or the like is mixed, onto a surface of the gypsum model; producing thereby a body having a shape which is fitted to an external shape of the ceramics frame or the ceramics abutment; heating to the specified temperature by the specified heating rate so as to remove the organic content; and baking. In this method, there can be taken the steps of producing a body having a shape which is fitted to an external shape of the ceramics frame or the ceramics abutment by an injection molding, an extrusion molding or a slip casting method; heating up to the specified temperature by the specified heating rate so as to remove the organic content; and baking.

After the dental ceramics material which is fitted to an external shape of the ceramics frame or the ceramics abutment is produced, a transparent porcelain material for baking is built on the surface of the dental ceramics material so as to have an external shape of a desired dental prosthesis, and then the dental ceramics material is baked again. By this process, a desired dental prosthesis model can be produced.

EXAMPLE

Example 1

A pink coloring agent was produced beforehand by dissolving 40 weight parts manganese oxide in 60 weight parts aluminum oxide as a solid solution by stirring and heating.

A yellow coloring agent was produced beforehand by dissolving 5 weight parts vanadium oxide in 95 weight parts zirconium oxide as a solid solution by stirring and heating.

A green body was obtained by: mixing 0.3 weight parts pink coloring agent and 0.6 weight parts yellow coloring agent with the primary material, which contains 5 weight parts yttrium oxide as the stabilizer, 94 weight parts zirconium oxide and 0.2 weight parts aluminum oxide; adding 5 wt. % binder of acrylic acid ester to the mixture; stirring again; and pressing to form the green body. Then, the ceramics frame for a molar was produced by: heating the green body up to 700 degrees C. at a rate of 100 degrees C./hour so as to degrease it; pre-baking at 1,150 degrees C.; attaching to the specific pedestal of the CAD/CAM device; machining to have shape of the ceramics frame for the molar; and baking at 1,500 degrees C. for 2 hours. The ceramics frame was colored having a color tone which was approximately similar to that of dentin of a tooth.

The "VITA VM9" (a baking porcelain material for a ceramic, produced by Vita Corporation) was built on the ceramics frame for the molar so as to have a color tone of A3, and baked at 960 degrees C. so as to produce a crown for a molar. The color tone was approximately similar to that of a tooth of a patient.

Example 2

A pink coloring agent was produced beforehand by dissolving 40 weight parts manganese oxide in 60 weight parts aluminum oxide as a solid solution by stirring and heating.

A yellow coloring agent was produced beforehand by dissolving 5 weight parts vanadium oxide in 95 weight parts zirconium oxide as a solid solution by stirring and heating.

A green body was obtained by: mixing 0.3 weight parts pink coloring agent and 0.6 weight parts yellow coloring agent with the primary material, which contains 5 weight parts yttrium oxide as the stabilizer, 94 weight parts zirconium oxide and 0.2 weight parts aluminum oxide; adding 5 wt. % binder of acrylic acid ester to the mixture; stirring again; and pressing to form the green body. Then, a ceramics frame for a front tooth was produced by: heating the green body up to 700 degrees C. at a rate of 100 degrees C./hour so as to degrease it; baking at 1,500 degrees C. for 2 hours; and attaching it to the specific pedestal of the CAD/CAM device. The ceramics frame was colored having a color tone which was approximately similar to that of dentin of a tooth.

The "VITA VM9" (a baking porcelain material for a ceramic, produced by Vita Corporation) was built on the ceramics frame for the front tooth so as to have the color tone of A3.5, and baked at 960 degrees C. so as to produce a crown for a molar. The color tone was approximately similar to that of a tooth of a patient.

What is claimed is:

1. A production method of a dental ceramics material, the method comprising:
    mixing a pink coloring agent and a yellow coloring agent at a mixing ratio of 0.001 to 5 wt. % respectively with zirconium oxide containing a stabilizer, where the pink coloring agent is obtained by dissolving manganese oxide in aluminum oxide as a solid solution, and the yellow coloring agent is obtained by dissolving vanadium oxide in zirconium oxide as a solid solution; and
    baking it so as to produce a dental ceramics material.

2. The production method of a dental ceramics material as claimed in claim 1,
    wherein the zirconium oxide containing the stabilizer contains aluminum oxide, and the content of the aluminum oxide is 0.1 to 30 wt. %.

3. The production method of a dental ceramics material as claimed in claim 1,
    wherein the stabilizer is one or more kinds selected from a group consisting yttrium oxide, magnesium oxide, calcium oxide, and cerium oxide, and the content thereof is 3 to 7 wt. %.

4. The production method of a dental ceramics material as claimed in claim 2,
    wherein the stabilizer is one or more kinds selected from a group consisting yttrium oxide, magnesium oxide, calcium oxide, and cerium oxide, and the content thereof is 3 to 7 wt. %.

* * * * *